US008796332B2

(12) United States Patent
Schlievert et al.

(10) Patent No.: US 8,796,332 B2
(45) Date of Patent: Aug. 5, 2014

(54) COMPOSITIONS AND METHODS FOR CONTROLLING INFECTIONS

(75) Inventors: Patrick M. Schlievert, Edina, MN (US); Marnie L. Peterson, Golden Valley, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1151 days.

(21) Appl. No.: 11/195,239

(22) Filed: Aug. 2, 2005

(65) Prior Publication Data

US 2006/0029558 A1    Feb. 9, 2006

Related U.S. Application Data

(60) Provisional application No. 60/598,240, filed on Aug. 3, 2004.

(51) Int. Cl.
*A01N 37/02* (2006.01)

(52) U.S. Cl.
USPC ........................................................ 514/546

(58) Field of Classification Search
None
See application file for complete search history.

(56) References Cited

U.S. PATENT DOCUMENTS

| | | | |
|---|---|---|---|
| 5,141,953 A * | 8/1992 | Parenti et al. ................. | 514/455 |
| 5,208,257 A | 5/1993 | Kabara | |
| 5,460,802 A | 10/1995 | Asami et al. | |
| 5,547,677 A | 8/1996 | Wright | |
| 5,549,901 A * | 8/1996 | Wright .......................... | 424/401 |
| 5,550,145 A | 8/1996 | Olund et al. | |
| 6,596,763 B1 * | 7/2003 | Thormar et al. .............. | 514/506 |
| 2005/0215634 A1 | 9/2005 | Schlievert et al. | |
| 2006/0029558 A1 | 2/2006 | Schlievert et al. | |

FOREIGN PATENT DOCUMENTS

| | | |
|---|---|---|
| EP | 0483812 A1 | 5/1992 |
| EP | 0483835 A1 | 5/1992 |
| JP | 2-502915 | 9/1990 |
| JP | 03-244349 | 10/1991 |
| JP | 11-079988 | 3/1999 |
| JP | 2001-501181 | 1/2001 |
| WO | WO 89/06124 | 7/1989 |
| WO | WO90/15601 A1 | 12/1990 |
| WO | WO95/31956 A1 | 11/1995 |
| WO | WO 97/25032 | 7/1997 |
| WO | WO 98/09520 | 3/1998 |

OTHER PUBLICATIONS

Bergsson et al., "In Vitro Killing of Candida Albicans by Fatty Acids and Monoglycerides", Antimicrob. Agents Chemother., 45 (11):3209-3212 (Nov. 2001).

Haynes et al., "Synergism between the Antifungal Agents Amphotericin B and Alkyl Glycerol Ethers" Antimicrob. Agents Chemother., 45 (7):1523-1529 (Jul. 1994).
Kabara et al., "Fatty Acids and Derivatives as Antimicrobial Agents", Antimicrob. Agents Chemother. 2(1):23-28 (Jul. 1972).
Bergsson et al., "In Vitro Killing of *Candida albicans* by Fatty Acids and Monoglycerides", Antimicrobial Agents and Chemotherapy, American Society for Microbiology, 45(11):3209-3212, Nov. 2001.
Brown-Skrobot, S.K. et al., "Tampon Additives and Toxic Shock Syndrome Toxin-1 (TSST-1) Production", Abstracts of the General Meeting of the American Society for Microbiology, 91:28, B-18, 1991.
Geshinizgani, A. et al., "Effect of Glycerol Monolaurate (GML) on Vaginal Microflora", Abstracts of the General Meeting of the American Society for Microbiology, 92:244, 1-45, 1992.
Haynes et al., "Synergism between the Antifungal Agents Amphotericin B and Alkyl Glycerol Ethers" Antimicrob. Agents Chemother., 38(7):1523-1529 (Jul. 1994).
Kabara et al., "Fatty Acids and Derivatives as Antimicrobial Agents", Antimicrobial Agents and Chemotherapy, 2(1): Jul. 23-28, 1972.
Kabara, J.J., "Antimicrobial Agents Derived from Fatty Acids", J. Amer. Oil Chem. Soc., 61(2):397-403, Feb. 1984.
Melish, M. et al., "Glycerol Monolaurate (GML) in Model Toxic Shock Syndrome (TSS)", Abstracts of the General Meeting of the American Society for Microbiology, 91:28, B-19, 1991.
Parsonnet, J. et al., "Affect of Glycerol Monolaurate on Multiplication of Gram-Positive and Gram-Negative Bacteria and Production of Toxic Shock Syndrome Toxin-I (TSST-1) by *S. aureus*", Abstracts of the General Meeting of the American Society for Microbiology, 92:50, B-148, 1992.
Projan, S.J., et al., "Glycerol Monolaurate Inhibits the Production of Toxic Shock Syndrome Toxin-1 and Alpha Hemolysin at the Level of Transcription", Abstracts of the General Meeting of the American Society for Microbiology, 92:50, B-147, 1992.
Quimby, F. et al., "Effect of the Surfactant, Glycerol Monolaurate (GML), on *Staphylococcus aureus* Growth and TSST-I Toxin Production on Catamenial Agents in Vivo", Abstracts of the General Meeting of the American Society for Microbiology, 91: 28, B-17, 1991.
Ross, R.A. et al., "The Effect of Glycerol Monolaurate (GML) on a Mixed Population of Vaginal Isolates Cultured in an In Vitro Model of the Vaginal Environment", Abstracts of the General Meeting of the American Society for Microbiology, 94: 323, N-43, 1994.
Schlievert, P.M. et al., "Effect of Glycerol Monolaurate on Bacterial Growth and Toxin Production", Antimicrobial Agents and Chemotherapy, 36(.3): 626-631, Mar. 1992.
Office Action mailed Nov. 17, 2008 in U.S. Appl. No. 10/986,512, 19 pages.
Office Action mailed Sep. 17, 2009 in U.S. Appl. No. 10/986,512, 16 pages.
Office Action mailed Jun. 24, 2011 in U.S. Appl. No. 10/986,512, 21 pages.
Office Action mailed May 8, 2012 in U.S. Appl. No. 10/986,512, 19 pages.
International Preliminary Report on Patentability; Feb. 15, 2007; World Intellectual Property Organization (WIPO) (International Bureau of); PCT/US2005/027608; 8 pages.

(Continued)

*Primary Examiner* — Michael Burkhart
(74) *Attorney, Agent, or Firm* — Fish & Richardson P.C.

(57) ABSTRACT

The invention features methods of inhibiting the growth of, or killing, fungal and certain bacterial microorganisms with one or more of a family of glycerol-based compounds.

12 Claims, 4 Drawing Sheets

(56) References Cited

OTHER PUBLICATIONS

International Search Report and Written Opinion; May 16, 2006; World Intellectual Property Organization (WIPO) (International Bureau of); PCT/US2005/27608; 13 pages.

Aucouturier et al., "Adjuvants designed for veterinary and human vaccines," *Vaccine*, 19:2666-2672, 2001.

Cook et al., "Clue cells in bacterial vaginosis: immunofluorescent identification of the adherent gram-negative bacteria as *Gardnerella vaginalis*," J Infect Dis., 160(3):490-496, Sep 1989 [Abstract only].

Cope, "A diffusible cytotoxin of *Haemophilus ducreyi*," Proc Natl Acad Sci USA., 94(8):4056-4061, Apr. 1997.

Cutter et al., "Antimicrobial activity of cetylpyridinium chloride washes against pathogenic bacteria on beef surfaces," J Food Prot., 63(5):593-600, May 2000.

Marsh, "Microbiological aspects of the chemical control of plaque and gingivitis," J Dent Res., 71(7):1431-1438, Jul. 1992.

Pitten, Frank-Albert et al., Efficacy of Cetylpyridinium Chloride Used as Oropharyngeal Antiseptic, Arzneim.-Forsch./Drug Res. 51 (II), 588-595 (2001).

"*Treponema pallidum*," Microbewiki [online] last modified Apr. 22, 2011 [retrieved on Jun. 10, 2013]. Retrieved from the Internet <URL: http://microbewiki.kenyon.edu/index.php/Treponema_pallidum>, 6 pages.

* cited by examiner

COMPOSITIONS AND METHODS FOR CONTROLLING INFECTIONS

This application claims the benefit of U.S. Provisional Application No. 60/598,240, filed Aug. 3, 2004. The disclosure of U.S. Provisional Application No. 60/598,240 is incorporated herein by reference in its entirety.

TECHNICAL FIELD

This invention relates to controlling infections, and more particularly to controlling fungal and certain bacterial infections.

BACKGROUND

Microbial infection continues to be an important problem, and therefore it is crucial that effective new therapeutic and/or prophylactic anti-microbial agents that are both inexpensive and logistically simple to deliver to appropriate subjects continue to be developed.

The disclosure of U.S. application Ser. No. 10/986,512 is incorporated herein by reference in its entirety.

SUMMARY

The invention is based in part upon the inventors' discovery that contact of yeasts and bacteria of a variety of strains with glycerol monolaurate (GML) curtailed their growth or killed them. In light of these factors, GML and related molecules are likely to be effective therapeutic or prophylactic agents against infections involving fungi and certain bacterial microorganisms. GML and related compounds are simple and inexpensive to produce in large amounts, transport, and administer to relevant subjects.

The invention provides a method of treatment or prophylaxis. The method includes: (a) identifying a subject likely to have been, or likely to be, exposed to an infectious fungal microorganism or an infectious bacterial microorganism, the bacterial microorganism being of a genus selected from the group consisting of Gardnerella, Haemophilus, Bacteroides, Bordetella, Fusobacterium, Prevotella, Porphyromonas, Atopobium, Mobiluncus, Peptostreptococcus, Mycoplasma, and Ureaplasma; and (b) administering to the subject an isolated glycerol-based compound (e.g., GML) that (i) kills or inhibits the growth of the infectious microorganism and (ii) is a glycerol-based compound containing a structure that is:

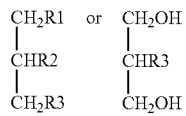

and
R1 can be: OH; $CO(CH_2)_8CH_3$; $CO(CH_2)_9CH_3$; $CO(CH_2)_{10}CH_3$; $CO(CH_2)_{11}CH_3$; $CO(CH_2)_{12}CH_3$; $O(CH_2)_9CH_3$; $O(CH_2)_{10}CH_3$; $O(CH_2)_{10}CH_3$; $O(CH_2)_{11}CH_3$; $O(CH_2)_{12}CH_3$; or $O(CH_2)_{13}CH_3$,
R2 can be: OH; $CO(CH_2)_8CH_3$; $CO(CH_2)_9CH_3$; $CO(CH_2)_{10}CH_3$; $CO(CH_2)_{11}CH_3$; $CO(CH_2)_{12}CH_3$; $O(CH_2)_9CH_3$; $O(CH_2)_{10}CH_3$; $O(CH_2)_{11}CH_3$; $O(CH_2)_{12}CH_3$; or $O(CH_2)_{13}CH_3$, and
R3 can be: $CO(CH_2)_8CH_3$; $CO(CH_2)_9CH_3$; $CO(CH_2)_{10}CH_3$; $CO(CH_2)_{11}CH_3$; $CO(CH_2)_{12}CH_3$; $O(CH_2)_9CH_3$; $O(CH_2)_{10}CH_3$; $O(CH_2)_{11}CH_3$; $O(CH_2)_{12}CH_3$; or $O(CH_2)_{13}CH_3$.

In this method, the infectious fungal microorganism can be any of a variety of yeasts, e.g., Candida species fungi (e.g., Candida albicans, Candida tropicalis, Candida parapsilosis, Candida glabrata, Candida krusei, Candida pseudotropicalis, Candida lusitaniae, or Candida guilliermondi), Cryptococcus species fungi (e.g., Cryptococcus neoformans), or the yeast phases of dimorphic fungi. Dimorphic fungi include, e.g., the above Candida species, Histoplasma capsulatum, Blastomyces dermatitidis, Paracoccidioides brasiliensis, Coccidioides immitis, or Sporothrix schenckii. The method can be applied to the hyphal phase as well as the yeast phases of these dimorphic fungi. Infectious fungal microorganisms can also be monomorphic fungi, for example, dermatophytes (ringworms), Pneumocystis carinii, Zygomycetes, Malassezia furfur, Fusarium species fungi, Cladosporium species fungi, Pseudoallescheria boydii, Penicillium species fungi (e.g., Penicillium marneffei, Penicillium chrysogenum, or Penicillium citrinum), or Aspergillus species fungi (e.g., Aspergillus fumigatus, Aspergillus flavus, or Aspergillus niger).

The subject can be any vertebrate (e.g., mammalian) subject recited herein, e.g., a human. The sites of infection can be, for example, systemic or in one or more organs (e.g., kidney, brain, lungs, eyes, intestine, or heart), tissues (e.g., skin, mucosal tissue, or sinuses,), bodily fluids (e.g., blood, cerebrospinal fluid, lymph, urine, semen, or amniotic fluid) or cavities (e.g., peritoneal, pleural, or pericardial).

The subject can have an infection, or be predisposed to an infection, with any of the infectious microorganisms listed in this document. In particular, such predisposition to infection can be a result of one or more of the following conditions: a compromised immune system (e.g., neutropenia, acquired immune deficiency syndrome (AIDS)), immunosuppression for cell, tissue, or organ transplantation, cancer (e.g., lymphoma, leukemia, or breast cancer), and therapy for cancer (e.g., radiation or chemotherapy).

The glycerol-based compounds (e.g., GML) can be administered either before, simultaneous with, or after the administration of one or more supplementary agents. Supplementary agents can include, for example, anti-fungal agents, modulators of immune function, or antibiotics.

Also embodied by the invention is an in vitro method of killing or inhibiting the growth of a fungal microorganism, or a bacterial microorganism, that involves culturing the microorganism with an isolated glycerol-based compound (e.g., GML). The glycerol-based compound can be any of those listed above. The glycerol-based compound can inhibit the growth of the microorganism or kill the microorganism. The microorganism can be any of those recited herein.

The invention also embodies a composition of one or more pharmaceutical excipients and one or more of any of the above glycerol-based compounds (e.g., GML).

In such compositions, the compounds can be dispersed in a solvent, e.g., in the form of a solution or a suspension. Pharmaceutical excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), ethylenediaminetetraacetic acid (EDTA), sodium chloride, liposomes, glucose, mannitol, sorbitol, glycerol, or a glycol such as propylene glycol or polyethylene glycol. Compositions containing one or more pharmaceutical excipients and one or more glycerol-based compounds or one or more glycerol-based compounds alone can also be included in suppositories, soaps, shampoos, gels, creams, foams, cosmetics, toothpastes, spermicidal compositions, acne medications.

The term "isolated compound" as used herein refers to a compound (e.g., GML or a related compound) that either has no naturally-occurring counterpart or has been separated or purified from components which naturally accompany it, e.g., in tissues such as pancreas, liver, spleen, ovary, testis, muscle, joint tissue, neural tissue, gastrointestinal tissue or tumor tissue, or body fluids such as blood, serum, or urine. Typically, a naturally occurring biological compound is considered "isolated" when it is at least 70%, by dry weight, free from other naturally-occurring organic molecules with which it is naturally associated. Preferably, a preparation of a compound for use in the invention is at least 80%, more preferably at least 90%, and most preferably at least 99%, by dry weight, that compound. The degree of isolation or purity can be measured by any appropriate method, e.g., column chromatography, polyacrylamide gel electrophoresis, or HPLC analysis. Since a compound (e.g., GML) that is chemically synthesized is, by its nature, separated from the components that naturally accompany it, the synthetic compound is by definition "isolated."

Isolated compounds, and supplementary agents useful for the invention, can be obtained, for example, by: (i) extraction from a natural source (e.g., from tissues or bodily fluids); (ii) where the compound or supplementary agents are proteins, by expression of recombinant nucleic acids encoding the proteins; or (iii) by standard chemical synthetic methods known to those in the art.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. All publications, patent applications, patents, and other references mentioned herein are incorporated by reference in their entirety. The materials, methods, and examples disclosed herein are illustrative only and not intended to be limiting.

Other features and advantages of the invention, e.g., treating fungal and certain bacterial infections, will be apparent from the following description and from the claims.

DETAILED DESCRIPTION

Figure 1:
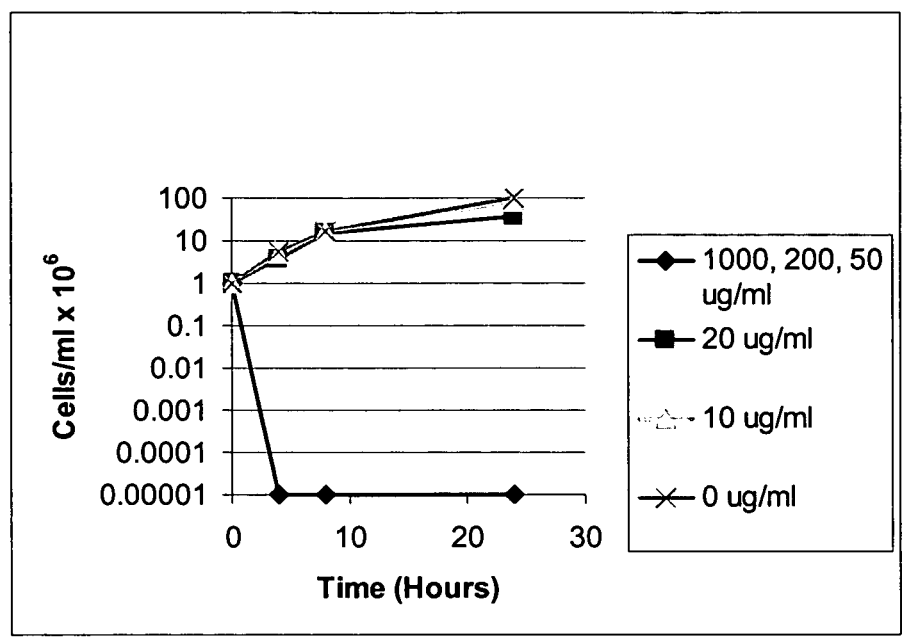
FIG. 1 is a line graph showing the effect of various concentrations of GML on the growth at various times of a first clinical isolate of *Candida albicans*.

The experiments of the inventors outlined in the Summary section indicate that GML kills and/or inhibits the growth of a variety of clinical isolates of *Candida* species and bacteria. Thus, it seems that GML and related compounds may limit, or even ablate, infection in a vertebrate subject by fungal and certain bacterial microorganisms and thus can be effective therapeutic and/or prophylactic agents against infection by fungal microorganisms.

Earlier work indicated that bacteria, and in particular *Staphylococcus aureus* and *Neisseria gonorrheae*, were relatively resistant to direct toxic effects of GML (see U.S. application Ser. No. 10/986,512, the disclosure of which is incorporated herein by reference in its entirety). The inventors have more recently found that certain gram negative *Enterobacteriaceae* (such as *Salmonella* and *Escherichia coli*) and a species of *Lactobacillus* (*L. crispatis*) are also relatively resistant to direct toxicity by GML. Thus, GML at concentrations up to 50 µg/ml had no effect on the in vitro growth of *L. crispatis* bacteria and, at concentrations up to 100 µg/ml, delayed (but did not stop) its growth. Indeed GML at the latter concentrations appeared to stabilize the bacteria in that it extended their stationary phase survival. Thus, it was surprising to discover that a number of other bacterial genera (see below) were highly sensitive to the direct toxic effects of GML.

While the invention is not limited by any particular mechanism of action, potential mechanisms by which GML and related compounds exert direct toxic effects on microorganisms include, without limitation, (a) direct cytotoxicity; (b) regulating microbial genes which cause the microorganisms to become more susceptible to cellular death (e.g., apoptosis); or (c) inhibiting processes of sexual or asexual reproduction, hyphae formation, spore formation, or any stage of the microorganism's life cycle. Direct toxic effects do not include those which require the participation of a non-microbial (e.g., host organism) cell. Indirect effects of GML and related compounds involving the participation of such non-microbial cells are described in detail in U.S. application Ser. No. 10/986,512, the disclosure of which is incorporated herein by reference in its entirety.

Various aspects of the invention are discussed below.
Methods of Killing or Inhibiting the Growth of Microorganisms These methods of the invention essentially involve contacting any of a variety of fungal or bacterial microorganisms with GML or related compounds so as to kill and/or inhibit the growth of such microorganisms.

In this method, infectious fungal microorganisms include any of a variety of yeasts, e.g., *Candida* species fungi (e.g., *Candida albicans*, *Candida tropicalis*, *Candida parapsilosis*, *Candida glabrata*, *Candida krusei*, *Candida pseudotropicalis*, *Candida lusitaniae*, or *Candida guilliermondi*), *Cryptococcus* species fungi (e.g., *Cryptococcus neoformans*), or the yeast phases of dimorphic fungi. Dimorphic fungi include, e.g., the above *Candida* species, *Histoplasma capsulatum*, *Blastomyces dermatitidis*, *Paracoccidioides brasiliensis*, *Coccidioides immitis*, or *Sporothrix schenckii*. The method can be applied to the hyphal phase as well as the yeast phases of these dimorphic fungi. Infectious fungal microorganisms can also be monomorphic fungi, for example, dermatophytes (ringworms), *Pneumocystis carinii*, Zygomycetes, *Malassezia furfur*, *Fusarium* species fungi, *Cladosporium* species fungi, *Pseudoallescheria boydii*, *Penicillium* species fungi (e.g., *Penicillium marneffei*, *Penicillium chrysogenum*, or *Penicillium citrinum*), or *Aspergillus* species fungi (e.g., *Aspergillus fumigatus*, *Aspergillus flavus*, or *Aspergillus niger*).

Bacteria of interest are *Gardnerella vaginalis*, *Haemophilus influenzae*, *Haemophilus ducreyi*, *Haemophilus aegyptius* (a variety of *Haemophilus influenzae*), *Haemophilus parainfluenzae*, *Haemophilus hemolyticus*, *Haemophilus suis*, *Bordetella pertussis* (related to *Haemophilus*), *Bordetella parap-* ertussis, Bordetella bronchoseptica, Bacteroides bacteria (e.g., *B. fragilis, B. thetaiotaomicron, B. vulgatus, B. ovatus, B. distasonis, B. uniformis, B. stercoris, B. eggerthii, B. merdae,* and *B. caccae*), *Prevotella melaninogenica* (previously designated *Bacteroides melaninogenicus*) and other *Prevotella* species (e.g., *P. bivia, P. buccae, P. corporis, P. dentalis, P. denticola, P. disiens, P. enoeca, P. heparinolytica, P. intermedia, P. loeschii, P. nigrescens, P. oralis, P. oris, P. oulora, P. tannerae, P. venoralis,* and *P. zoogleoformans*), *Fusobacterium* bacteria (e.g., *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans,* and *F. varium*), *Porphyromonas* bacteria (e.g., *P. asaccharolytica, P. cangingivalis, P. canoris, P. cansulci, P. catoniae, P. circumdentaria, P. crevioricanis, P. endodontalis, P. gingivalis, P. gingivicanis, P. gulae, P. levii, P. macacae, P. salivosa*), *Atopobium* bacteria (e.g., *A. fossor, A. minutum, A. parvulum, A. rimae,* and *A. vaginae*), *Mobiluncus* bacteria (e.g., *M. curtisii* (including subspecies *curtisii* and *holmesii*), and *M. mulieris*), *Peptostreptococcus* bacteria (e.g., *P. anaerobius, P. asaccharolyticus, P. harei, P. hydrogenalis, P. indoliticus, P. ivorii, P. lacrimalis, P. lactolyticus, P. magnus, P. micros, P. octavius, P. prevotii, P. trisimilis, P. tetradius,* and *P. vaginalis*), *Mycoplasma* bacteria (e.g., *M. pneumonia, M. buccale, M. faucium, M. fermentans, M. salivarium, M. arthriditis, M. hominis, M. orale, M. genitalium, M. penetrans, M. lipophilum, M. laidlawii, M. pirum, M. pulmonis, M. mycoides, M. gallisepticum, M. hyopneumoniae,* and *M. mobile*), and *Ureaplasma* bacteria (e.g., *U. urealyticum* and *U. parvum*).

The compounds that can be used to kill and/or inhibit the growth of the microorganims include GML and a variety of glycerol-based compounds related to GML. The compounds include fatty acid esters of glycerol in which the alcohol group on one, or both, of the terminal carbon atoms of glycerol, the alcohol group on only the middle carbon atom, the alcohol groups on the middle carbon atom and one of the terminal carbon atoms, or the alcohol groups on all three carbon atoms are esterified with fatty acids. The fatty acids can be 10 carbon, 11 carbon, 12 carbon, 13 carbon, or 14 carbon linear alkyl fatty acid esters and can be present in the molecule in any combination. In addition, instead of being linked to the glycerol backbone by ester linkages, 10 carbon, 11 carbon, 12 carbon, 13 carbon, or 14 carbon linear alkyl chains can be linked to it by ether linkages.

In summary, the inhibitory glycerol-based compounds useful in the invention include the following:

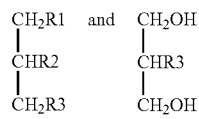

in which R1 is: OH; $CO(CH_2)_8CH_3$; $CO(CH_2)_9CH_3$; $CO(CH_2)_{10}CH_3$; $CO(CH_2)_{11}CH_3$; $CO(CH_2)_{12}CH_3$; $O(CH_2)_9CH_3$; $O(CH_2)_{10}CH_3$; $O(CH_2)_{11}CH_3$; $O(CH_2)_{12}CH_3$; or $O(CH_2)_{13}CH_3$, R2 is: OH; $CO(CH_2)_8CH_3$; $CO(CH_2)_9CH_3$; $CO(CH_2)_{10}CH_3$; $CO(CH_2)_{11}CH_3$; $CO(CH_2)_{12}CH_3$; $O(CH_2)_9CH_3$; $O(CH_2)_{10}CH_3$; $O(CH_2)_{11}CH_3$; $O(CH_2)_{12}CH_3$; or $O(CH_2)_{13}CH_3$, and R3 is: $CO(CH_2)_8CH_3$; $CO(CH_2)_9CH_3$; $CO(CH_2)_{10}CH_3$; $CO(CH_2)_{11}CH_3$; $CO(CH_2)_{12}CH_3$; $O(CH_2)_9CH_3$; $O(CH_2)_{10}CH_3$; $O(CH_2)_{11}CH_3$; $O(CH_2)_{12}CH_3$; or $O(CH_2)_{13}CH_3$.

Thus, examples of useful compounds include GML, glycerol ester-linked to monolaurate, glycerol dilaurate, glycerol monocaprylate, glycerol monocaprate, glycerol monomyristate, and glycerol monopalmitate.

Additional inhibitor compounds useful in the invention include, for example: (a) phosphatidyl choline and phosphatidyl ethanolamine, and (b) sphingolipids such as ceramides. In these compounds, the fatty acids (or corresponding ether-linked linear alkyl chains) are any of those described above.

Compounds useful in the method are those that kill or substantially inhibit the growth of infectious microorganisms of interest in vitro and/or in vivo. As used herein, "substantial inhibition of growth" means at least two-fold (e.g., at least: three-fold; four-fold; five-fold; six-fold; seven-fold; eight-fold; nine-fold; ten-fold; 25-fold; 50-fold; 100-fold; 1,000-fold; 10,000-fold; 100,000-fold, or even greater) inhibition of growth. In the case of in vivo methods, the killing or substantial inhibition of growth will generally be at a concentration of the inhibitory compound that is not fatally toxic to the host organism.

Inhibitory compounds useful for all the treatment methods described in this document can be used in the manufacture of medicaments for treatment of infections by any of the microorganisms listed herein.

One or more (e.g., two, three, four, five, six, seven, eight, nine, ten, 11, 12, 15, 18, 20, 25, 30, or more) of the above compounds can be delivered to a microorganism of interest, either alone, or with one or more (e.g., two, three, four, five, six, seven, eight, nine, ten, 11, 12, 15, 18, 20, 25, 30, or more) supplementary agents. Such supplementary agents include substances other than glycerol-based compounds that serve, for example, to kill and/or inhibit the growth of the microorganisms. Supplementary agents can also be antibiotics. Antimicrobial agents include, for example, anti-fungal agents belonging to the azole class (e.g., miconazole, fluconazole, or itraconazole), polyene class (e.g., nystatin, amphotericin B, or lipid formulations of amphotericin B), or echinocandins class (e.g., caspofungin). Anti-fungal agents can also be nucleoside analogues (e.g., flucytosine), allylamines (e.g, naftifine and terbinafine), griseofulvin, tolnaftate, or selenium compounds (e.g., selenium sulfide). Antibacterial antibiotics include, without limitation, the penicillins and other beta lactams, cephalosporins, glycopeptides (for example, vancomycin), aminoglycosides, tetracyclines, chloramphenicol, oxazolidinones, streptogramins, folate inhibitors, metronidazole, rifampin, macrolides, clindamycin, polymyxins, quinolones, and fluoroquinolones. Supplementary agents can also be cytokines (e.g., interferon α, β, or γ, monocyte chemoattactant protein-1, interleukins, macrophage inflammatory protein 3α, or GRO α, β, or γ) or any other modulators of immune function.

The methods of killing or, inhibiting the growth of, microorganisms can be in vitro or in vivo.

In vitro application of the methods of the invention can be useful in basic scientific studies of fungal or bacterial infection, mechanisms of fungal or bacterial growth and infection, and methods of controlling fungal or bacterial infection and/or inflammation. In the in vitro methods of the invention, one or more inhibitory compounds can be cultured with any of the microorganisms mentioned herein. Moreover, the in vitro methods can involve the addition of one or more glycerol-based compounds (e.g., GML) to a culture of non-microbial tissue or cells, e.g., mammalian cells, that is suspected of containing, or is at risk of becoming infected with, relevant fungal or bacterial microorganisms. In cultures containing such inhibitory compounds and non-microbial tissue or cells, the microorganisms can be within such non-microbial tissue or cells or present in the culture medium. Cultures of the invention can also be, for example, "positive controls" in screening assays for new inhibitory compounds. Measurements of, for example, the infectious microorganism titer or the level of cell proliferation/survival can be made after various times of incubation using methods known in the art. These in vitro systems can contain, in addition to inhibitory compounds, one or more of the supplementary agents described above. The in vitro methods also include those in which it is desired to prevent or inhibit microbial (e.g., yeast or bacterial) growth in appropriate cultures, e.g., cultures of mammalian cells.

As used herein, "prophylaxis" can mean complete prevention of the symptoms of a disease, a delay in onset of the symptoms of a disease, or a lessening in the severity of subsequently developed disease symptoms. As used herein, "therapy" can mean a complete abolishment of the symptoms of a disease or a decrease in the severity of the symptoms of the disease.

The methods of the invention can be applied to a wide range of species, e.g., humans, non-human primates, horses, cattle, pigs, sheep, goats, dogs, cats, rabbits, guinea pigs, hamsters, rats, mice, and birds such as chickens, turkeys and canaries.

In Vivo Approaches

The methods of the invention will preferably be in vivo. In certain embodiments, the method can employ two phases for evaluating GML or a related glycerol-based compound for treatment or prophylaxis of microbial (fungal or bacterial) infection, an initial in vitro phase and then an in vivo phase. GML or a related glycerol-based compound is administered to the microorganism in vitro, and if a change in the growth or quantity of the microorganism is noted, then the compound is further administered to a test animal in various amounts and evaluated for an effect of the compound on infection with the microorganism in the animal.

In a preferred in vivo approach, one or more of the isolated compounds is administered to the subject. In addition, one or more of the above-described supplementary agents can be administered together with, or separate from, the inhibitory compounds. Where the supplementary agents are administered separately, they can be administered simultaneously with the compounds but by a different route. Alternatively, they can be administered at a different time from the inhibitory compounds and either by the same route or by a different route.

Generally, the compounds and supplementary agents are suspended in a pharmaceutically-acceptable carrier (e.g., physiological saline) and administered orally or by intravenous (i.v.) injection or infusion, or injected subcutaneously, intramuscularly, intrathecally, intraperitoneally, intrarectally (e.g., as a suppository), intravaginally, intranasally, intragastrically, intratracheally, or intrapulmonarily. They can, for example, be delivered directly to a site of infection, e.g., intrapulmonarily where the infection is of the lung (e.g., by inhalation). Moreover, the compounds can be administered topically. For topical application, the compounds can be incorporated into, for example, creams, gels, foams, cosmetics, shampoos, toothpastes, or bath soaps. They can be used in, for example, acne medications, in spermicidal compositions, e.g., gels, foams, or creams.

In glycerol-based compound compositions, the compounds can be dispersed in a solvent, e.g., in the form of a solution or a suspension. For example, they can be dispersed in an appropriate physiological solution, e.g., physiological saline. The compositions can also contain one or more pharmaceutical excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), ethylenediaminetetraacetic acid (EDTA), sodium chloride, liposomes, glucose, mannitol, sorbitol, glycerol, or a glycol such as propylene glycol or polyethylene glycol. Solutions or suspensions can be encapsulated in liposomes or biodegradable microspheres. Suitable preservatives include benzalkonium chloride, methyl- or propyl-paraben, and chlorobutanol. Pharmaceutical formulations are known in the art, see, for example, Gennaro Alphonso, ed., *Remington's Pharmaceutical Sciences,* 18$^{th}$ Ed., (1990) Mack Publishing Company, Easton, Pa.

The dosages of the inhibitory compounds and supplementary agents to be used depend on the choice of the route of administration; the nature of the formulation; the nature of the patient's illness; the subject's size, weight, surface area, age, and sex; other drugs being administered; and the judgment of the attending physician. Suitable dosages are generally in the range of 0.0001-100.0 mg/kg. Wide variations in the needed dosage are to be expected in view of the variety of compounds and supplementary agents available and the differing efficiencies of various routes of administration. For example, oral administration would be expected to require higher dosages than administration by i.v. injection. Variations in these dosage levels can be adjusted using standard empirical routines for optimization as is well understood in the art. Administrations of compounds and/or supplementary agents can be single or multiple (e.g., 2-, 3-, 4-, 6-, 8-, 10-, 20-, 50-, 100-, 150-, or more fold). Encapsulation of the compounds and/or supplementary agents in suitable delivery vehicles (e.g., polymeric microparticles or implantable devices) may increase the efficiency of delivery.

GML and glycerol-based compounds can be useful for the treatment of various forms of fungal and bacterial infection. In one aspect, GML and related compounds can be useful for the treatment of, e.g., mucocutaneous candidiasis, which includes, for example, oropharyngeal candidiasis (thrush), gastrointestinal candidiasis (involving the mucosa of the stomach and small and large intestine), or cutaneous candidiasis (e.g., intertrigo involving areas of the axillae, gluteal, inframmary folds, and groin). GML and related glycerol-based compounds can be especially useful for the treatment of vaginal infections such as vaginal candidiasis, the most common *Candida* mucocutaneous infection in women, especially in association with pregnancy, oral contraceptives, antibiotic therapy, diabetes, and HIV.

It has been known for more than a century that the dominant microflora of the normal, healthy human vagina are members of the *Lactobacillus acidophilus* group. In 1987, a genotypic analysis of the dominant flora confirmed this finding with the identification of *L. crispatis, L. gasseri,* and *L. jensenii* and one unknown *Lactobacillus* as the dominant species [Giorgi et al. (1987) Microbiologica 10:377-384]. In 1999, DNA-based studies confirmed these findings. A more recent study identified this group as the predominant organisms, but also identified *L. iners* as a dominant species [Zhou et al. (2004) Microbiology 150:2565-2573]. These organisms are low G+C gram positive bacteria, like the streptococci, and are completely dependent on fermentation of glucose to lactic acid, normally as a single product but occasionally together with acetic acid, ethanol, and carbon dioxide. The production of lactic acid is thought to maintain vaginal pH between 4.0 and 4.5 at times other than menstruation, making it difficult for potential pathogens to grow. The sheer numbers of these flora that occupy nearly all mucosal surface space contribute to interference with establishment of pathogens. In addition, as aerotolerant anaerobes, the lactobacilli produce superoxide and then convert superoxide to hydrogen peroxide as part of their normal metabolism; by definition, lactobacilli lack catalase to convert hydrogen peroxide to oxygen and water. Hydrogen peroxide is thought to further restrict colonization by pathogens. Moreover, there is evidence that lactobacilli produce bacteriocins and surfactants that restrict growth of potential pathogens [Soledad et al. (2000) Microbes Infect. 2:543-546]. Unpublished studies of the inventors suggest that lactobacilli are themselves susceptible to inhibition of growth by acid accumulation and hydrogen peroxide but their occupation of the surfaces adjacent to buffered human tissue likely maintains a favorable growth environment for them. Vaginal alterations in pH and hydrogen peroxide are predictive of overgrowth of organisms such as *Gardnerella, Bacteroides*, and *Candida*, though the exact mechanisms leading to pH and hydrogen peroxide alterations are unclear.

Bacterial vaginosis (BV) is a syndrome in which the vaginal flora becomes altered such that *Lactobacillus* species no longer dominate [Forsum et al. (2005) APMIS 113:81-90]. BV is characterized by overgrowth of organisms such as *Gardnerella vaginalis*, some anaerobes, and *Mycoplasma hominis*. More recent studies suggest newly recognized vaginal organisms such as Atopobium species may be associated with BV [Verstraelen et al. (2004) Am J. Obstet. and Gynecol. 191:1130-1132, incorporated herein by reference in its entirety]. The anaerobes associated with BV include *Bacteroides, Prevotella, Peptostreptococcus*, and *Morbiluncus* species [Forsum et al. (2005), supra, incorporated herein by reference in its entirety]. In studies of pregnant women, both asymptomatic and symptomatic BV patients were found to have a 10-fold or higher increase in these organisms, particularly Gardnerella. Symptomatic women have 100- to 1000-fold increases in *Gardnerella* bacteria and anaerobes. In such patients there is a concomitant drop in lactobacilli, and for unknown reasons, the lactobacilli that are present make less hydrogen peroxide that their normal counterparts. The amine product trimethylamine is a metabolic product of bacterial overgrowth and its fishy odor is indicative of BV. Factors that have been associated with BV include sexual activity, particularly new sexual partners, antibiotic use, reduction for unknown reasons of pH, and use of IUDs (intrauterine devices) [Hawes et al. (1996) J. Infect. Dis. 190:1374-1381]. Approximately one half of BV patients are asymptomatic. Persistent vaginal inflammation is associated with BV.

The clinical diagnosis of BV is based on having three of the four of the following characteristics in vaginal discharges: (1) pH above 4.5; (2) a thin skim milk appearance; (3) a fishy amine odor when 10% potassium hydroxide is placed on the discharge; and (4) clue cells [Amsel et al. (1983) Am. J. Med. 74:14-22]. Clue cells are vaginal cells that are so covered with bacteria that their borders are obscured. On microscopic examination of vaginal discharges from patients with BV, long lactobacilli morphotypes are seen to be diminished.

Pregnant women with BV have 50% to 100% increases in preterm, low birth-weight deliveries, amniotic fluid infections, and chorioamnion infections [Hillier et al. (1995) N. Engl. J. Med. 333:1737-1742]. The high concentration of potentially virulent microbes also predisposes the upper genital tract to infections, including postpartum endometritis after cesarean delivery, pelvic inflammatory disease following therapeutic abortion, and vaginal cuff cellulitis following abdominal hysterectomy.

Treatment options for BV include metronidazole (orally) and clindamycin (topically) in non-pregnant women and metronidazole in symptomatic pregnant women as first line treatment regimens. For recurrent BV, regular treatment and then biweekly suppressive doses of metronidazole are recommended. *Lactobacillus* given orally or intravaginally may help, though it effectiveness is still in debate.

*Candida albicans* is the most common fungal pathogen affecting humans, including being a common cause of vulvovaginitis [Fidel (2004) Trends Microbiol. 12:220-227, incorporated herein by reference in its entirety]. There are nearly 20 species of *Candida* capable of causing human infections, but *C. albicans* causes 85% to 90% of infections. *C. albicans* is often seen morphologically in its yeast form, but the organism has the ability to grow in tissues as pseuodohyphal and hyphal forms as well as yeasts. *C. albicans* may be isolated from skin, mouth, rectum, and vagina of many humans. The organism is only recently being extensively studied for its pathogenesis factors [Calderone et al (2001) Trends Microbiol. 9:327-335]. The organism has both the ability to convert from yeast to more resistant hyphal and pseudohyphal forms rapidly and the ability to adhere to epithelial and endothelial cells. Immune avoidance mechanisms have been described. The organism makes proteases and phospholipases that may facilitate invasion. Possibly the most significant traits that lead to infections are perturbations in the host. Factors such as host treatment with antimicrobial compounds, altered pH through use of oral contraceptives or for unknown reasons, pregnancy, immune response differences among women, diabetes, and age have been linked to increased infection.

Vulvovaginal candidiasis (VVC) is a common fungal infection both in normal women and women with immune deficiencies. The infection causes vaginal itching, and a thick vaginal discharge. Erythema is usually present as evidence of significant inflammation. Recurrent VVC is defined as the presence of infection with three to four episodes per year [Sobel et al. (1998) Am J. Obstet. Gynecol. 2:543-546]. Although the exact mechanisms that predispose to recurrent infection are unknown, hypotheses include: (1) deficiencies for unknown reasons in normal flora; (2) deficiencies in Th1 cell activation and/or over-activation of Th2 cells; and (3) acquired hypersensitivity to *Candida*. Treatment options for VVC include use of a variety of topical agents or oral azoles for non-recurrent infection, and persistent oral azoles for recurrent disease.

Application of the methods of the invention can be particularly useful in the therapy and/or prophylaxis to opportunistic infections. The opportunistic infections can be a result of use of antibiotics (both prophylactic and therapeutic) as well as immunosuppressive and cytotoxic drugs; indwelling foreign bodies, including prosthetic heart valves, prosthetic joints, and intravascular monitoring devices; venous, arterial, urinary, and peritoneal catheters; and organ, cell, or tissue transplantation. Subjects with a compromised immune system are also predisposed to infection (e.g., fungal infection) and stand to benefit from this invention. Such subjects can have one or more of the following conditions: deficiency of neutrophils (neutropenic), deficiency of T-cells (lymphopenic), mucous membrane toxicity, or any one or several of a group of immune disorders (e.g., chronic granulomatous disease, Job's syndrome, AIDS, and other T-cell deficiencies). Subjects can also have one or more of a variety of cancers, including, without limitation, lymphoma, leukemia, or breast cancer. Such subjects can have undergone or can be undergoing cancer treatment (e.g., radiotherapy, chemotherapy, gene therapy, immunotherapy, angiogenesis therapy, donor cell transplantation or infusion, or stem cell therapy).

In another aspect, GML and related compounds can be useful for the treatment of deep-organ candidiasis and deep-organ infections by any of the other microorganisms listed herein. Deep-organ infections of interest include, without limitation, hepatosplenic candidiasis, ocular candidiasis, candidemia, renal candidiasis, cardiac candidiasis, central nervous system candidiasis, and musculoskeletal candidiasis, as well as corresponding infections by any of the other microorganisms listed herein.

Methods to test whether a particular regimen is therapeutic for, or prophylactic against, a particular disease are known in the art. Where a therapeutic effect is being tested, a test population displaying symptoms of the disease (e.g., humans or experimental animals having a Candida infection) is treated with a test regimen involving any of the above-described strategies. A control population, also displaying symptoms of the disease, is treated, with a placebo or a different regimen. Disappearance or a decrease of the disease symptoms in the test subjects would indicate that the test regimen is an effective therapeutic methodology.

By applying the same strategies to subjects prior to onset of disease symptoms (e.g., experimental animals prior to deliberate infection with Candida albicans), test regimens can be tested for efficacy as prophylactic methodologies. In this situation, prevention of, or delay in, onset of disease symptoms is tested.

A number of embodiments of the invention have been described. Nevertheless, it will be understood that various modifications may be made without departing from the spirit and scope of the invention.

The following examples are meant to illustrate, not limit, the invention.

EXAMPLES

Example 1

Materials and Methods

Yeast Phase Cultures

The *Candida albicans* samples that were tested in the experiments described in Examples 2 and 3 were recent clinical isolates. The strains were of low passage and were maintained on Todd Hewitt (Difco Laboratories, Detroit, Mich.) agar plates. The organisms were transferred to 25 ml Todd Hewitt broth cultures in 125 ml Erlenmeyer flasks and grown overnight at 37° C. in 7% $CO_2$ with shaking at 200 revolutions per minute (RPM). The next morning the organisms were transferred to new 125 ml flasks containing 25 ml Todd Hewitt medium at a final concentration of $1\times10^6$ colony forming units (CFU)/ml. At the same time various concentrations of GML were added to the flasks to achieve concentrations of 0 to 1000 µg/ml, specifically 0, 10, 20, 50, 200, and 1000 µg/ml. The GML was made up at a concentration of 100,000 µg/ml in absolute ethanol for addition to the flasks. A volume of ethanol, corresponding to the volume of GML/ethanol solution added to achieve a GML concentration of 1000 µg/ml, was added to the control flasks containing 0 µg/mL of GML to insure that the diluent did not account for the activity. The flasks were cultured for up to 24 hours at 37° C. in 7% $CO_2$ with shaking at 200 revolutions per minute. At time points of 4, 8 and 24 hours, dilutions of the cultures were made and CFU/ml were determined after plating onto Todd Hewitt agar plates. This experiment was performed twice.

Hyphal Phase Cultures

*Candida albicans* microorganisms were cultured on a Todd Hewitt agar plate for 48 hours at 37° C. in the presence of 7% $CO_2$ to promote growth of hyphal forms. This plate was used to streak the microorganisms for isolation on Todd Hewitt agar plates containing 0, 10, 20, 50, or 100 µg/mL of GML. The plates were incubated for 48 hours and examined for *Candida* growth. The experiment was done in duplicate plates. The results obtained with duplicate plates were the same.

Example 2

Effect of GML on Yeast Phase *Candida* Growth

Figure 2:
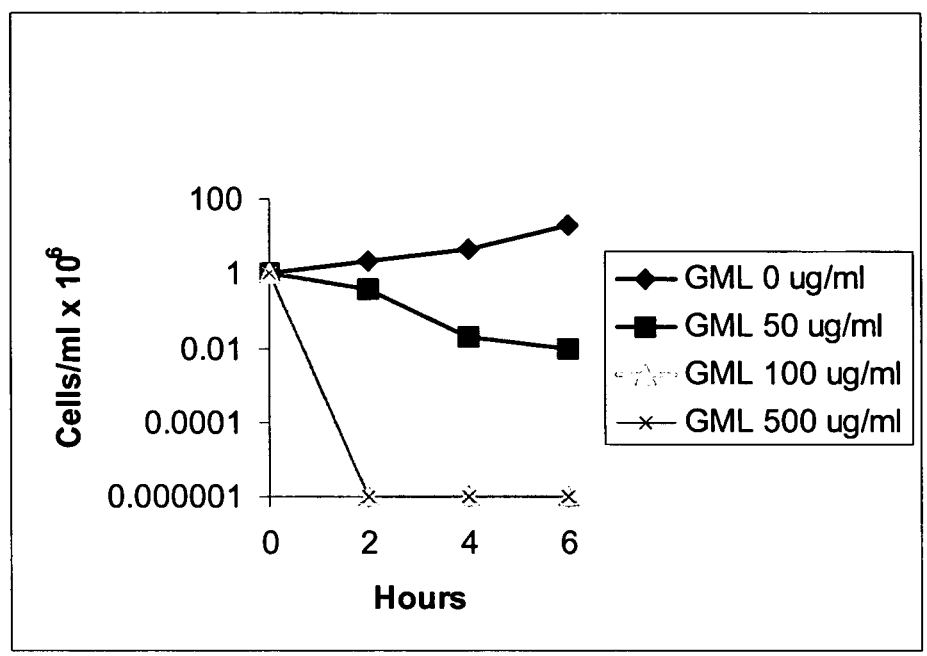
FIG. 2 is a line graph showing the effect of various concentrations of GML on the growth at various times of a second clinical isolate of *Candida albicans*.

The effect of growing yeast phase organisms of a clinical isolate of *Candida albicans* in the presence of GML was tested in liquid cultures as described in Example 1. As shown in FIG. 1, by 4 hours of incubation, no organisms were detectable in cultures that contained 50, 200, and 1000 µg/ml of GML, representing more than a 5 log reduction in CFU/ml. The GML-mediated killing effect was not seen in cultures containing 20 and 10 µg/ml of GML. In these cultures the microorganisms grew to almost the same level as in the control cultures. The experiment was repeated with identical results. The experiment was also carried out with a second clinical isolate of *Candida albicans*. As shown in FIG. 2, by 2 hours of incubation, no organisms were detectable in cultures that contained 100 and 500 µg/ml of GML. In the culture containing 50 µg/ml of GML, the number of organisms present in the culture was reduced at all time intervals sampled (e.g., 2, 4, and 6 hours) compared to the culture containing 0 µg/ml of GML.

Example 3

Effect of GML on Hyphal Phase *Candida* Growth

Organisms (at the hyphal phase) of 11 clinical isolates of *Candida albicans* were separately streaked on Todd Hewitt agar plates containing various concentrations of GML. The experiments were performed in duplicate. After 48 hours of culture in the presence of GML, the strains failed to grow on plates containing GML at 50 and 100 µg/ml concentrations. In contrast, the organisms grew on plates containing 0, 10 and 20 µg/ml.

Example 4

Growth Inhibition by GML of Other Clinical Isolates of *Candida albicans*

Figure 3:
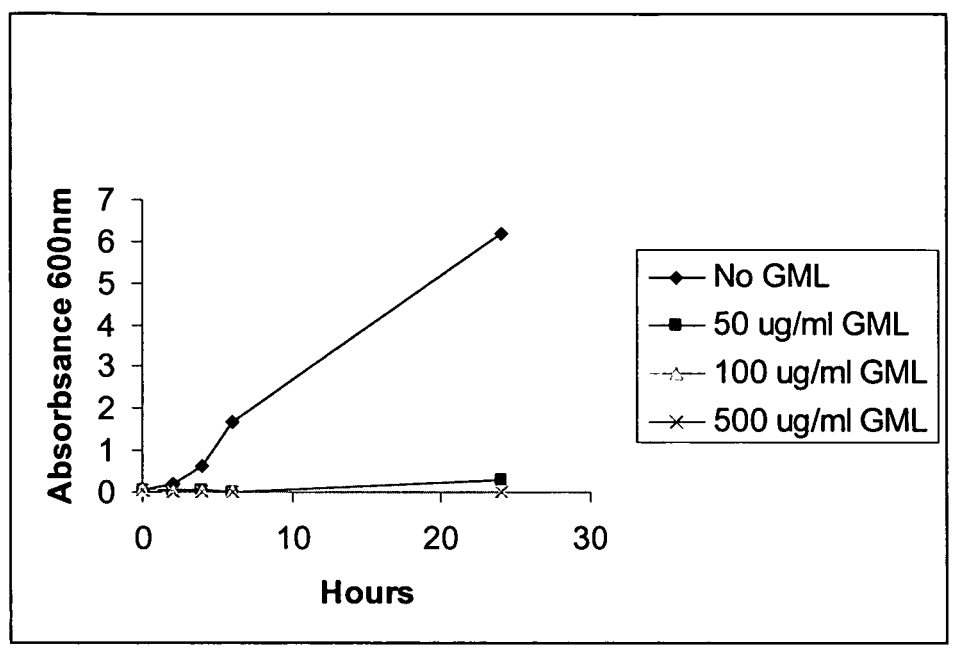
FIG. 3 is a line graph showing the effect of various concentrations of GML on the growth at various times of *Candida albicans*. The data shown are the means of values obtained with five different clinical isolates of *Candida albicans*.

Five clinical isolates of *Candida albicans* (separate from those tested in experiments described in Example 2) were tested for susceptibility to growth inhibition by GML. The data in FIG. 3 are the means of values obtained by separately testing each of the five clinical isolates. The experiments were performed in liquid culture as described in Example 2 except that, instead of measuring the number of organisms in the cultures by plating on agar plates, values of absorbance at 600 nm were determined at the indicated time points. An absorbance value of 6.5 corresponds to about $5\times10^8$ CFU/ml of *Candida albicans*. The growth of all of the isolates was inhibited by GML. Culturing for 6 hours 0.1 ml aliquots of the isolates (containing about $10^6$ CFU/ml) in 100 µg/ml and 500 µg/ml of GML yielded an average of about 700 CFU/ml and about 400 CFU/ml, respectively.

Example 5

Effect of GML on Mycelium Formation of *Aspergillus* and *Penicillium* Fungi

Organisms (at the spore phase) of *Aspergillus* and *Penicillium* fungi obtained from nature were separately streaked on Todd Hewitt agar plates containing various concentrations of GML. The plates were incubated at room temperature for 36 hours after which mycelium growth was determined by direct visual examination. Both *Aspergillus* and *Penicillium* fungi failed to grow on plates containing GML at 100 and 500 μg/ml concentrations. In contrast, the organisms grew on plates containing 0 and 50 μg/ml. At about 4 days after incubation, there were still no visible colonies on plates containing GML at 100 and 500 μg/ml, whereas in plates containing GML at 0 and 50 μg/ml, the colonies were larger in size compared to cultures incubated for 36 hours.

Organisms of *Aspergillus* and *Penicillium* fungi were differentiated by their distinct characteristics.

*Aspergillus* organisms appear as white molds with peppery-colored spores. The spores come off the conidiophore in chains, a feature that serves as a diagnostic characteristic.

*Penicillium* organisms appear as molds with a blue-green-colored arial mycelium, while the rest of the mold is white. The mold produces penicillin which appears as a yellow pigment and diffuses into the agar. Conidia can be seen in small numbers of chains coming from the conidiophore, a diagnostic property of *Penicillium*.

Example 6

Growth Inhibition by GML of *Garnerella vaginalis*, *Haemophilus influenzae*, and *Bacteroides fragilis* Bacteria Cells ($1.2 \times 10^7$/ml in a total volume of 25 ml of dialyzable beef heart medium) of a recent clinical isolate of the gram negative rod *Gardnerella vaginalis* in vitro were cultured for various lengths of time with various concentrations of GML. At the various time points, the concentration of bacteria in the cultures were determined by colony counting on chocolate agar plates. Data obtained at the 6 and 24 hour time points are shown in Table 1. GML at concentrations as low as 5 μg/ml were bactericidal to *G. vaginalis*. GML was also effective in inhibiting the growth of *G. vaginalis* under the same culture condition and the same medium but supplemented with of fetal calf serum Table 2). This finding points to the likely efficacy of GML in vivo. Moreover, GML (5 μg/ml or greater) inhibited growth of *G. vaginalis* plated (0.1 ml at $1.2 \times 10^7$/ml) onto chocolate agar plates (Table 3; data obtained after 24 hours of culturing).

TABLE 1

Inhibition of *G. vaginalis* growth by GML.

| GML Concentration (μg/ml) | Cells/ml ($\times 10^7$) at 6 hours | Cells/ml ($\times 10^7$) at 24 hours |
| --- | --- | --- |
| 0 | 15 | 230 |
| 1 | 13 | 208 |
| 5 | 0.0002 | 0.0004 |
| 10 | <0.000001 | <0.000001 |
| 20 | <0.000001 | <0.000001 |
| 50 | <0.000001 | <0.000001 |
| 100 | <0.000001 | <0.000001 |
| 1000 | <0.000001 | <0.000001 |

TABLE 2

Inhibition of *G. vaginalis* growth by GML in the presence of 10% fetal calf serum.

| GML Concentration (μg/ml) | Cells/ml ($\times 10^7$) at 24 hours |
| --- | --- |
| 0 | 225 |
| 1 | 210 |
| 5 | 201 |
| 10 | 160 |
| 20 | 88 |
| 50 | 1.8 |
| 100 | <0.03 |

TABLE 3

Inhibition of *Gardnerella vaginalis* growth on chocolate agar plates by GML.

| GML Concentration (μg/ml) | Growth Characteristics |
| --- | --- |
| 0 | Confluent growth |
| 1 | Confluent growth |
| 5 | No visible growth |
| 10 | No visible growth |
| 20 | No visible growth |
| 50 | No visible growth |
| 100 | No visible growth |

*G. vaginalis* was formerly designated *Haemophilus vaginalis*. This consideration raised the possibility that GML would inhibit the growth of *Haemophilus influenzae*. Two recent clinical isolates of encapsulated (capsule type not typable) *Haemophilus influenzae* (0.1 ml at $1.0 \times 10^7$/ml plated) organisms were tested for ability to grow on chocolate agar plates with no or various concentrations of GML (Table 4; data obtained after 24 of culture). The growth of both strains was inhibited at GML concentrations of 10 μg/ml or greater.

TABLE 4

Inhibition of growth of two clinical isolates of *Haemophilus influenzae* strains by GML.

| GML Concentration (μg/ml) | Growth Characteristics (Strain 1) | Growth Characteristics (Strain 2) |
| --- | --- | --- |
| 0 | Confluent growth | Confluent growth |
| 1 | Confluent growth | Confluent growth |
| 5 | Confluent growth | Confluent growth |
| 10 | No visible growth | No visible growth |
| 20 | No visible growth | No visible growth |
| 50 | No visible growth | No visible growth |
| 100 | No visible growth | No visible growth |

Figure 4:
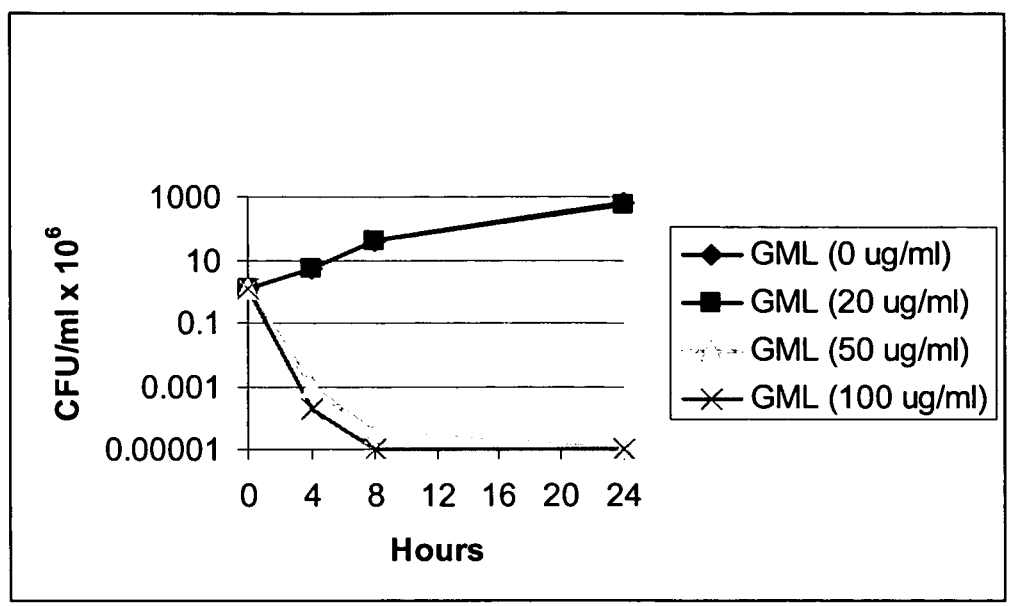
FIG. 4 is a line graph showing the effect of various concentrations of GML on the growth at various times of a clinical isolate of *Haemophilus influenzae*.

FIG. 4 shows the results of a kinetic study using one of the *Haemophilus influenzae* strains tested in the experiment described above. The strain was inoculated (at a concentration of $1.2 \times 10^6$ CFU/ml) into 50 ml of Todd Hewitt medium containing various concentrations of GML. The cultures were grown for 24 hours in an atmosphere of 7% carbon dioxide (balance air) with shaking at 100 RPM. At designated times samples were removed, and colony forming units (CFU) per milliliter were determined by plate counts on chocolate agar plates. GML at 50 μg/ml or 100 μg/ml inhibited the growth of the *H. influenza* organisms.

The kinetics of growth-inhibition by GML of the obligate gram negative anaerobe *Bacteroides fragilis* ATCC 25285 was determined. An overnight culture of *B. fragilis* ATCC 25285 in Wilkens Chalgren (WC) broth was inoculated into fresh media (WC) to give a starting cell concentration of $1\times10^7$ cells/ml. Cultures containing no or various concentrations of GML were incubated in an anaerobic chamber for 4.5 and 24 hours at which time the concentrations of bacteria were determined by plate colony counting (Table 5). GML at 50 and 100 μg/ml inhibited the growth of the *B. fragilis* bacteria. GML (at 20 μg/ml) inhibited growth such that the relevant culture contained at least 1,000 fold fewer bacteria than the control culture at 4.5 hours; regrowth was observed at 24 hours of culture. Because growth of *B. fragilis* was inhibited by GML, it is expected that growth of the related gram negative anaerobe, *Prevotella*, would also be inhibited by GML.

TABLE 5

Inhibition of growth of *Bacteroides fragilis* by GML.

| Experimental Condition | Cells/ml × $10^7$ at 4.5 hours | Cells/ml × $10^7$ at 25 hours |
|---|---|---|
| Control | 12 | 154 |
| GML 1 μg/ml | 16 | 130 |
| GML 10 μg/ml | 1.4 | 150 |
| GML 20 μg/ml | <0.01 | 200 |
| GML 50 μg/ml | <0.01 | <10 |
| GML 100 μg/ml | <0.001 | <10 |

A number of embodiments of the invention have been described. Nevertheless, it will be understood that various modifications may be made without departing from the spirit and scope of the invention. Accordingly, other embodiments are within the scope of the following claims.

What is claimed is:

1. A method of treatment or prophylaxis of a bacterial vaginosis infection in a subject in need thereof, wherein the bacterial vaginosis infection is caused by a bacterial microorganism of the genus *Gardnerella*, the method comprising:
   administering to the subject a composition comprising an effective amount of glycerol monolaurate (GML) and one or more pharmaceutical excipients,
   wherein the subject has been exposed to a bacterial microorganism of the genus *Gardnerella* and the GML is administered to the subject at a dosage of 0.0001-100 mg/kg.

2. The method of claim 1, wherein the subject is a vertebrate.

3. The method of claim 2, wherein the vertebrate is a mammal.

4. The method of claim 3, wherein the mammal is a human.

5. The method of claim 1, further comprising: before, simultaneous with, or after the administration of the glycerol monolaurate (GML), administering one or more supplementary agents.

6. The method of claim 5, wherein the one or more supplementary agents are antibiotics.

7. The method of claim 1, wherein the *Gardnerella* bacterial microorganism is a *Gardnerella vaginalis* bacterial microorganism.

8. The method of claim 1, wherein the one or more pharmaceutical excipients comprises ethylenediaminetetraacetic acid (EDTA).

9. The method of claim 1, wherein the one or more pharmaceutical excipients comprises ascorbic acid.

10. The method of claim 1, wherein the one or more pharmaceutical excipients comprises propylene glycol.

11. The method of claim 1, wherein the one or more pharmaceutical excipients comprises polyethylene glycol.

12. The method of claim 1, wherein the one or more supplementary agents comprises *Lactobacillus*.

* * * * *